US00PP37729P2

(12) United States Plant Patent
Jhe

(10) Patent No.: US PP37,729 P2
(45) Date of Patent: Oct. 6, 2026

(54) ***MICHAELMOELLERIA* PLANT NAMED 'SAPPHIRE'**

(50) Latin Name: *Michaelmoelleria vietnamensis*
Varietal Denomination: SAPPHIRE

(71) Applicant: Flores Laeti, Den Hoorn (NL)

(72) Inventor: Chen Shih Jhe, Linluo Township (TW)

(73) Assignee: Flores Laeti (NL)

( * ) Notice: Subject to any disclaimer, the term of this patent is extended or adjusted under 35 U.S.C. 154(b) by 0 days.

(21) Appl. No.: 19/351,724

(22) Filed: Oct. 7, 2025

(51) Int. Cl.
*A01H 5/02* (2018.01)
*A01H 6/44* (2018.01)

(52) U.S. Cl.
USPC ..... Plt./263.1

(58) Field of Classification Search
USPC ..... Plt./263.1
See application file for complete search history.

*Primary Examiner* — Karen M Redden

(57) ABSTRACT

A new and distinct cultivar of *Michaelmoelleria* plant named 'SAPPHIRE' is disclosed, characterized by ovate, variegated leaves with three different colors, silver, light green and dark green. Variegation comes in both blotchy and somewhat linear shapes. Plants are compact and non-leggy, having short internodes. Violet colored flowers are held above the softly pubescent foliage. The new cultivar is a *Michaelmoelleria*, normally used for indoor ornamental purposes.

2 Drawing Sheets

Latin name of the genus and species: *Michaelmoelleria vietnamensis.*

Cultivar denomination: 'SAPPHIRE'.

BACKGROUND OF THE INVENTION

The new *Michaelmoelleria* cultivar is the result of a naturally occurring whole plant mutation of an unnamed, unpatented *Michaelmoelleria vietnamensis. Michaelmoelleria* 'SAPPHIRE' was found and selected by the inventor in a nursery in Linlua Township, Pingtung County, Taiwan in December of 2023.

Asexual reproduction of the new cultivar has been performed by both vegetative cuttings and tissue culture. Asexual reproduction was first performed at the same nursery Pingtung County, Taiwan in December of 2023 using vegetative cuttings. This propagation and subsequent tissue culture propagation have shown that the unique features of this cultivar are stable and reproduced true to type in multiple successive generations.

SUMMARY OF THE INVENTION

The cultivar 'SAPPHIRE' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'SAPPHIRE' These characteristics in combination distinguish 'SAPPHIRE' as a new and distinct *Michaelmoelleria* cultivar:

1. Ovate, variegated leaves with three different colors, silver, light green and dark green.
2. Both blotchy and somewhat linear variegation shapes.
3. Compact, non-leggy growth with short internodes.
4. Violet flowers held above the foliage.

5. Softly pubescent foliage.
6. Side shoot production, creating a fuller, bushier plant.

PARENT COMPARISON

Plants of the new cultivar *Michaelmoelleria* 'SAPPHIRE' are similar to plants of the parent in most horticultural characteristics; however, plants of the new cultivar 'SAPPHIRE' differ in the following:

1. Foliage color of the new cultivar is dark green, light green and silver. Foliage color of the parent variety is dark green with creamy white variegation. The overall effect is a more muted contrasting variegation.
2. The new cultivar has variegation over about roughly 60% of the leaf; the parent has variegation over roughly 20% of the leaf.
3. Plants of the new cultivar produce more side shoots (20-30% more) and grow more slowly than plants of the parent.
4. Foliage of the new cultivar is about 20% smaller than foliage of the parent.

COMMERCIAL COMPARISONS

*Michaelmoelleria* 'SAPPHIRE' may be compared to the Gesneriad *Streptocarpus* 'Pretty Turtle', unpatented. The plants share main horticultural characteristics, however, 'SAPPHIRE' differs in the following:

1. 'SAPPHIRE' has smaller foliage by about 30% which is ovate, compared to the very round foliage of 'Pretty Turtle'.
2. Foliage of 'SAPPHIRE' is not as susceptible to breaking and tearing as foliage of 'Pretty Turtle'.
3. Silver-white veining of 'Pretty Turtle' occurs throughout the foliage and bleeds significantly into the leaf blade. Vein coloration of 'SAPPHIRE' is dark green. The silver and light green variegation of 'SAPPHIRE' occurs as irregular blotches on the leaf blade.

4. Leaf margins of 'SAPPHIRE' are entire; leaf margins of 'Pretty Turtle' are crenate or serrate.
5. Flower color of 'SAPPHIRE' is violet, flower color of 'Pretty Turtle' lavender to magenta.
6. Plant habit of 'SAPPHIRE' is more mounded compared to the flattened habit of 'Pretty Turtle'.

BRIEF DESCRIPTION OF THE PHOTOGRAPHS

The accompanying photographs illustrate in full color a typical plant of the new cultivar, 'SAPPHIRE' grown in a greenhouse in Nantou County, Taiwan. The photographs were taken using conventional techniques and although colors may appear different from actual colors due to light reflectance it is as accurate as possible by conventional photographic techniques.

DETAILED BOTANICAL DESCRIPTION

Figure 1:
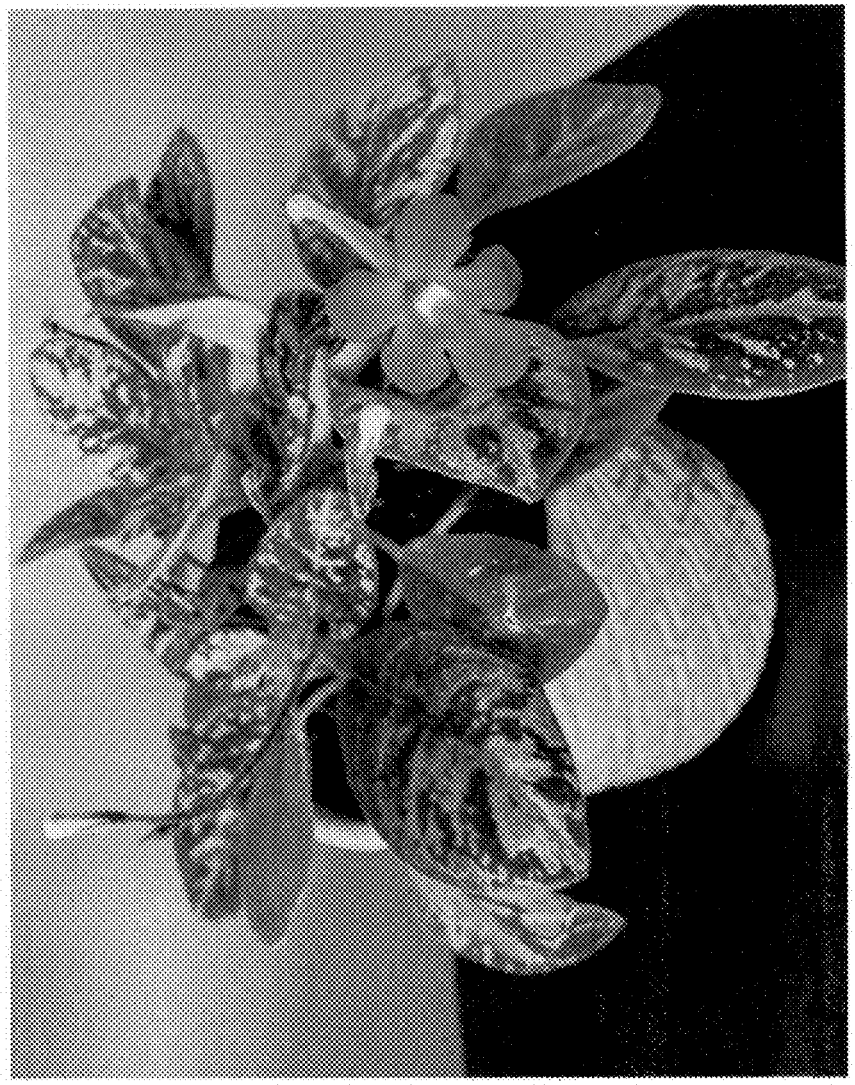
FIG. 1 illustrates a flowering plant 'SAPPHIRE'. The plant is approximately 4 months old from cuttings.
Figure 2:
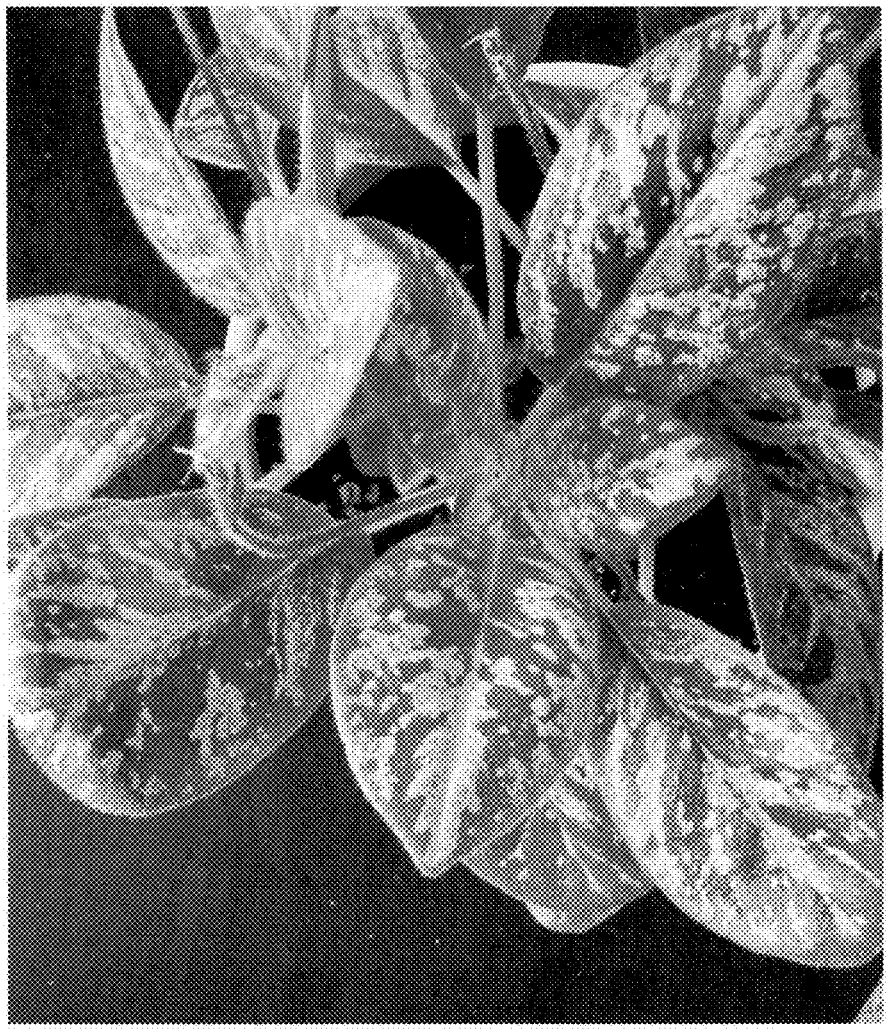
FIG. 2 illustrates a close-up view of the foliage.

In the following description, color references are made to The Royal Horticultural Society Colour Chart 6$^{th}$ Edition 2015 except where general terms of ordinary dictionary significance are used. The following observations and measurements describe 'SAPPHIRE' plants grown in a greenhouse in Vista, CA. The growing temperature ranged from approximately 20° C. to 25° C. during the day and from approximately 18° C. to 20° C. during the night. General light conditions are normal sunlight and numerical values represent averages of typical plant types.

Botanical classification: *Michaelmoelleria vietnamensis* 'SAPPHIRE'.

PROPAGATION

Typical method: Vegetatively propagated leaf cuttings.

Time to initiate roots: Approximately 3 to 4 weeks at approximately 20° C.

Time to produce a fully rooted plantlet: Approximately 18 weeks at approximately 20° C.

PLANT

Growth habit: Compact and mounding.

Age of the plant described: Approximately 4 months from a rooted cutting.

Pot size of plant described: 6 inch pot

Height: Approximately 10 cm from soil line to top of foliar plane. Approximately 15 cm to top of highest flower.

Plant spread: Approximately 28 cm at widest point.

Branching characteristics: Basal side shoots.

Stem length: 3 cm.

Stem diameter: 12 mm.

Stem color: Green 139D.

Stem texture: Densely pubescent.

Internode: 5 to 15 cm.

Roots: Very fine, white to light tan. Not accurately measured with The Colour Chart, as the soil stains the root coloration.

FOLIAGE

Leaf:

*Arrangement*.—Sub-opposite or irregularly whorled.

*Quantity*.—Average 20 to 28 leaves.

*Average length*.—Average range 6 to 9 cm excluding petiole.

*Average width*.—4 to 5.5 cm.

*Shape of blade*.—Ovate.

*Apex*.—Broad acute.

*Base*.—Broad attenuate or oblique.

*Margin*.—Entire.

*Appearance of top surface*.—Shiny.

*Appearance of top surface*.—Matte.

*Pubescence*.—Very dense, soft, about 1 mm hairs, densely covering top and bottom leaf surfaces.

*Aspect*.—Very slightly undulating, overall leaf reflexes downward in older foliage.

*Color*.—Young foliage upper side: Main color Green 137C. Blotchy, somewhat linear variegation Greyed-Green 192B covers about 25% to 40% of the surface and appears very shiny. Dark Yellow-Green 147A blotches center of leaf covers about 10% to 20% of the surface. Margin 3 to about 5 mm Green 137C. Young foliage under side: Greyed-Green 193A Mature foliage upper side: Main color Green 137C. Blotchy, somewhat linear variegation Greyed-Green 192B covers about 25% to 40% of the surface and appears very shiny. Dark Yellow-Green 147A blotches center of leaf covers about 10% to 20% of the surface. Margin 3 to about 5 mm Green 137C. Mature foliage under side: Greyed-Green 193A.

*Venation*.—Type: Pinnate. Venation color upper side: Yellow-Green 147C. Venation color under side: Green 138C.

*Petiole*.—Average Length: Average range 3.5 to 6 cm. Average Width: 4 to 5 mm. Texture: Densely and softly pubescent. Color: Green 139D. Upper surface very lightly flushed Greyed-Purple N187B when immature.

FLOWER

Natural flowering season: Continuous.

Inflorescence and flower type and habit: Individual occurring asymmetrical, single funnel shaped flowers. A second small bud appears about 1 cm below the main flower but quickly aborts.

Approximate quantity of flowers per plant: About 1 to 8 flowers and buds at one time.

Flowers persistent.

Individual flower bud:

*Shape*.—Tubular, with spherical apex.

Length.—3 cm.

*Diameter*.—Tube 5 mm, spherical apex 9 mm.

*Color*.—Green-White 157D lightly flushed 157A. Veins Greyed-Purple N187A.

Flowers:

*Flower length*.—5.8 cm.

*Flower width*.—3.0 cm.

*Corolla Upper petals* (*upper lip*).—Number: 2, fused together at base. Length: 1.7 cm. Width: 1.2 cm. Shape: Ovate. Apex: Obtuse. Margin: Entire. Texture: All surfaces glabrous. Appearance: All surfaces slightly shiny. Color: When opening: Inner surface: Upper ⅔ Violet N88A lightly flushed N87B. Lower ⅓ N88D. Very faint veins N87A. Outer surface: White N155A. Fully opened: Inner surface: Upper ⅓

Violet N88A lightly flushed N87B. Lower ⅔ N88D. Very faint veins N87A. Outer surface: White N155A.

*Corolla Lower petals* (*lower lip*).—Quantity: 3. Length: 2 cm. Width: 1.5 cm. Shape: Orbicular, fused at base. Apex shape: Obtuse. Margin: Shallow crenate, undulating. Texture: Velvety, all surfaces. Color: When opening: Inner surface: Upper ⅔ Violet N88A lightly flushed N87B. Lower ⅓ N88D. Very faint veins N87A. Outer surface: White N155A. Fully opened: Inner surface: Upper ⅓ Violet N88A lightly flushed N87B. Lower ⅔ N88D. Very faint veins N87A. Outer surface: White N155A.

*Tube*.—Length: 4 cm. Width: 10 mm, at widest point, 4 mm and narrowest point. Texture: Glabrous inner surface. Outer surface minutely pubescent. Color: When opening: Inner surface: Upper 1/2 Purple-Violet N80C heavily spotted Purple N79A. Lower ½ White N155B. Outer surface: White N155A flushed N81C. Fully opened: Inner surface: Upper ½ Purple-Violet N80D heavily spotted Purple N79AC. Lower ½ White N155B. Outer surface: White N155A flushed N81D.

*Throat*.—Diameter: 7 mm. Texture: Sparsely pubescent. Color: Yellow 3C. 2 lines of sparse faint dots Purple N79A.

Petaloids: None.

Sepals:

*Quantity*.—Average 5.

*Shape*.—Narrow deltate, base fused.

*Length*.—9 mm.

*Width*.—3 mm.

*Apex*.—Acute.

*Base*.—Fused.

*Margin*.—Entire.

*Texture*.—Highly pubescent, all surfaces.

*Color*.—Upper Surface: Yellow-Green 146C heavily flushed Greyed-Purple 183B. Lower Surface: Yellow-Green 147C.

Peduncle:

*Length*.—Average range 5 to 15 mm.

*Diameter*.—3 mm.

*Texture*.—Soft, dense pubescence.

*Color*.—Greyed-Red 182B flushed 183C.

*Angle of attachment*.—Approximately 30 to 45 degree angle from peduncle.

*Aspect*.—Arched.

*Strength*.—Fibrous and difficult to break.

REPRODUCTIVE ORGANS

Androecium:

Stamens:

*Number*.—4, diadiamous, 2 anthers.

*Filament length*.—Approximately 1 cm. Adnate or semi-adnate.

*Filament color*.—Purple-Violet N81D.

Anthers:

*Length*.—2.5 mm.

*Shape*.—Ovate.

*Color*.—Violet-Blue N92A.

*Pollen*.—Color: Greyed-Purple N187D. Quantity: Scant.

Gynoecium:

*Pistil*.—Number: 1. Length: Approximately 3.5 cm. Style: Length: Approximately 3.2 cm. Color: White N155C. Stigma: Shape: Bifurcate. Color: Purple N78C.

OTHER CHARACTERISTICS

Fruits and seeds: Not observed to date.

Disease/pest resistance: Neither resistance nor susceptibility to other normal diseases and pests of *Michaelmoelleria* observed.

Temperature range: USDA zones 9 to 11.

What is claimed is:

1. A new and distinct cultivar of *Michaelmoelleria* plant named ‘Sapphire’ as herein illustrated and described.

* * * * *